US009160985B2

(12) United States Patent
Endo et al.

(10) Patent No.: US 9,160,985 B2
(45) Date of Patent: Oct. 13, 2015

(54) WIRELESS IMAGE COMMUNICATION SYSTEM AND WIRELESS IMAGE COMMUNICATION APPARATUS

(71) Applicants:OLYMPUS CORPORATION, Tokyo (JP); OLYMPUS MEDICAL SYSTEMS CORP., Tokyo (JP)

(72) Inventors: Takahisa Endo, Hachioji (JP); Manabu Ishizeki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 220 days.

(21) Appl. No.: 13/749,036

(22) Filed: Jan. 24, 2013

(65) Prior Publication Data
US 2013/0137377 A1    May 30, 2013

Related U.S. Application Data

(63) Continuation of application No. PCT/JP2011/064716, filed on Jun. 27, 2011.

(30) Foreign Application Priority Data

Aug. 4, 2010  (JP) .................................. 2010-175485

(51) Int. Cl.
*H04B 7/24*  (2006.01)
*H04N 7/18*  (2006.01)
(Continued)

(52) U.S. Cl.
CPC ............ *H04N 7/183* (2013.01); *A61B 1/00016* (2013.01); *A61B 1/00059* (2013.01); *H04N 7/185* (2013.01); *H04N 2005/2255* (2013.01); *H04W 36/06* (2013.01)

(58) Field of Classification Search
CPC ......... H04B 1/40; H04N 7/183; H04N 7/185; A61B 17/12104; A61B 18/22; A61B 1/00165
USPC ........ 455/39, 509, 73, 78, 83, 91, 130, 277.1, 455/501, 63.1; 600/114, 129, 156, 182
See application file for complete search history.

(56) References Cited

U.S. PATENT DOCUMENTS

| 4,633,304 | A | 12/1986 | Nagasaki | |
| 8,730,988 | B2 * | 5/2014 | Kim et al. | 370/437 |

(Continued)

FOREIGN PATENT DOCUMENTS

| EP | 0 895 437 A2 | 2/1999 |
| EP | 1 732 278 A1 | 12/2006 |

(Continued)

OTHER PUBLICATIONS

International Search Report for PCT/JP2011/064716, mailing date of Jul. 19, 2011.

(Continued)

*Primary Examiner* — Tuan Pham
(74) *Attorney, Agent, or Firm* — Westerman, Hattori, Daniels & Adrian, LLP

(57) ABSTRACT

A wireless image communication system comprises a transmitter that wirelessly transmits image data and a receiver that receives the image data transmitted by the transmitter. The transmitter comprises: a communication channel change instruction unit that accepts, from an operator, an instruction to change a communication channel currently used in the wireless communication with the receiver for the transmission of the image data to a predetermined communication channel different from the currently used communication channel; and a transmitting unit that wirelessly transmits, on the basis of the instruction, information related to the predetermined communication channel to the receiver. The receiver comprises: a receiving unit that receives the information wirelessly transmitted by the transmitter; and a wireless communication control unit that performs a process to change the communication channel currently used in the wireless communication with the transmitter to the communication channel indicated by the received information.

6 Claims, 10 Drawing Sheets

(51) Int. Cl.
*A61B 1/00* (2006.01)
*H04N 5/225* (2006.01)
*H04W 36/06* (2009.01)

(56) References Cited

U.S. PATENT DOCUMENTS

2006/0217591 A1* 9/2006 Abe .............................. 600/118
2010/0296007 A1* 11/2010 Cooper ......................... 348/731

FOREIGN PATENT DOCUMENTS

| | | |
|---|---|---|
| JP | 60-048011 A | 3/1985 |
| JP | 07-050871 A | 2/1995 |
| JP | 2003-318768 A | 11/2003 |
| JP | 2005-341415 A | 12/2005 |
| WO | 2010/067862 A1 | 6/2010 |
| WO | 2010/143349 A1 | 12/2010 |
| WO | 2011/048914 A1 | 4/2011 |
| WO | 2011/049163 A1 | 4/2011 |

OTHER PUBLICATIONS

Extended European Search Report dated Mar. 3, 2014, issued in European Patent Application No. 11814385.8 (6 pages).

Japanese Office Action dated Nov. 25, 2014, issued in Japanese Application No. 2010-175485; w/English translation. (6 pages).

* cited by examiner

FIG. 12
| CH NO. (CH_NO) | COMMUNICATION CHANNEL GROUP ||
|---|---|---|
| | COMMUNICATION CHANNEL (PHYSICAL CHANNEL NUMBER) | ADJACENT CHANNEL (PHYSICAL CHANNEL NUMBER) |
| 1 | 1 | 2, 3, 4 |
| 2 | 6 | 3, 4, 5, 7, 8, 9 |
| 3 | 11 | 8, 9, 10, 12, 13 |
FIG. 13
| | | SCAN ORDER (SCAN_NO) ||||||||
|---|---|---|---|---|---|---|---|---|---|
| | | 1 | 2 | 3 | 4 | 5 | 6 | 7 | 8 |
| CH NO. (CH_NO) | 1 | 1 | 2 | 3 | 4 | 0 | 0 | 0 | 0 |
| | 2 | 6 | 3 | 4 | 5 | 7 | 8 | 9 | 0 |
| | 3 | 11 | 8 | 9 | 10 | 12 | 13 | 0 | 0 |
FIG. 14
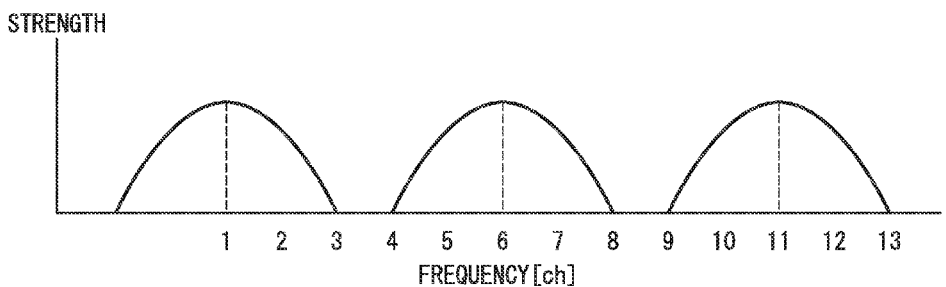
FIG. 15
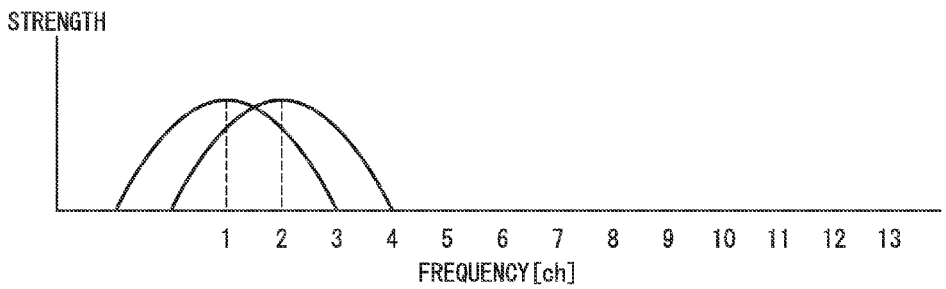

WIRELESS IMAGE COMMUNICATION SYSTEM AND WIRELESS IMAGE COMMUNICATION APPARATUS

CROSS REFERENCE TO RELATED APPLICATIONS

This application is a continuation application based on a PCT Patent Application No. PCT/JP2011/064716, filed Jun. 27, 2011, whose priority is claimed on Japanese Patent Application No. 2010-175485, filed on Aug. 4, 2010, the entire content of which are hereby incorporated by reference.

BACKGROUND OF THE INVENTION

Field of the Invention

The present invention relates to a wireless image communication system including a transmitter that transmits image data according to wireless communication using a wireless communication scheme such as a wireless local area network (LAN) and a receiver that receives the image data. In addition, the present invention relates to a wireless image communication apparatus that receives image data wirelessly transmitted from an external apparatus.

BACKGROUND ART

Description of the Related Art

In recent years, endoscopic apparatuses that enable a subject image of an inside of a body cavity or a conduit to be observed using a monitor by inserting an elongated insert member into the body cavity or the conduit have been widely used. In general, the above-described endoscopic apparatus includes an endoscope having the insert member to be inserted into the body cavity or the conduit and a main body apparatus having a light source apparatus or a video processor. The endoscope and the main body apparatus are connected by a light guide cable, which guides illumination light from the light source apparatus to the endoscope, and a signal cable, which transmits an image pickup signal obtained by the endoscope to the video processor. Thereby, a moving range of the endoscope is limited and the operability of the endoscope is hindered.

For example, in Japanese Unexamined Patent Application, First Publication, No. S60-48011, an illuminating apparatus constituted by a light emitting diode (LED) and the like is embedded in the endoscope, so that the light guide cable extending from the endoscope is removed. In addition, a video signal processing circuit, which obtains a video signal capable of being displayed on a monitor by performing video signal processing on an image pickup signal, and a transmitting circuit, which transmits the video signal by radio waves, are provided in the endoscope, and a receiving apparatus, which receives the radio waves and demodulates the video signal, is provided separately from the endoscope so that the signal cable extending from the endoscope is removed. In general, the above-described endoscopic apparatus is also referred to as a wireless endoscopic apparatus, and has an advantage in that the limitation of a moving range of the endoscope is mitigated and the operability thereof is improved.

Because the receiving apparatus is provided separately from the endoscope in the wireless endoscopic apparatus of the related art, it is necessary to set up a communication channel of the endoscope of a transmitting side according to a communication channel set in the receiving apparatus and establish a connection of wireless communication. A method of uniquely determining a combination of the receiving apparatus and the endoscope and fixedly pre-setting a communication channel to an arbitrary communication channel is also considerable. However, because disinfection/sterilization treatments and examinations of the endoscopes are simultaneously processed in a hospital using a plurality of receiving apparatuses and a plurality of endoscopes, the combination of the receiving apparatus and the endoscope is not uniquely determined. In order to prevent the interference of radio waves, it is necessary to set communication channels of the receiving apparatuses to be different from each other.

As a communication scheme for use in wireless communication, it is effective to use a wireless communication scheme such as Institute of Electrical and Electronics Engineers (IEEE) 802.11 for use in a wireless LAN in which high-speed data communication is possible. In this wireless communication scheme, the wireless communication is performed by selecting an arbitrary communication channel from a plurality of communication channels so as to effectively use a frequency band. As illustrated in FIG. 15, each communication channel is arranged so that part of a frequency band to be used overlaps that of another communication channel due to a limit of an available frequency band. Thus, at the initiation of an operation, the endoscopic apparatus determines an optimum communication channel by checking a use state of an available communication channel, and starts wireless communication of the endoscope with the receiving apparatus.

While the endoscopic apparatus performs communication of image data, there is an influence on transmission such as an increase in a probability of occurrence of a busy state of a communication channel and a decrease in a transmission rate when a use state of a communication channel determined at the initiation of communication, such as an abrupt increase in a communication data amount of another wireless terminal, has been changed during data communication, for example, according to the initiation of file transmission in a personal computer (PC) or the like. In addition, there is a problem in that a burst communication failure occurs and image noise occurs due to the use of an electrosurgical knife or the like in a place adjacent to a place in which the endoscopic apparatus has been installed.

On the other hand, in Japanese Unexamined Patent Application, First Publication, No. H7-50871, a mobile communication apparatus capable of changing a communication channel during communication has been proposed. When a communication channel switching command has been input according to a switch operation, the mobile communication apparatus changes a communication channel for use in data communication to a communication channel newly designated from a base station by executing a communication channel switching process. As a result, not only can the communication channel be automatically switched, but also the communication channel can be switched according to an operator's intention.

In Japanese Unexamined Patent Application, First Publication, No. H7-50871, because it is difficult to sense a burst communication failure, good communication may not be performed even when switching to a communication channel designated by the base station is performed. When the operator has recognized a use state of a communication channel and the like by peripheral wireless equipment, good communication is performed through switching to a communication channel, a communication state of which is determined by the operator himself/herself to be good, even when the burst communication failure occurs in a communication channel in use. However, in Patent Document 2, although the operator can provide an instruction to switch a communication channel, a new communication channel is designated by the base station. Thus, the operator's intention is not reflected to the selection of a communication channel after switching. Therefore, switching to a communication channel determined by the operator to have a good communication state is not necessarily performed.

SUMMARY

The present invention provides a wireless image communication system and a wireless image communication apparatus capable of changing a communication channel in use to a communication channel designated by an operator.

A wireless image communication system may include a transmitter that wirelessly transmits image data and a receiver that receives the image data transmitted from the transmitter. The transmitter may include: a communication channel change instruction unit configured to receive an instruction to change a communication channel, which is in use in wireless communication with the receiver related to transmission of the image data, to a predetermined communication channel different from the communication channel in use from an operator; and a transmitting unit configured to wirelessly transmit information regarding the predetermined communication channel based on the instruction to the receiver. The receiver may include: a receiving unit configured to receive the information wirelessly transmitted from the transmitter; and a wireless communication control unit configured to perform a process of changing the communication channel in use in the wireless communication with the transmitter to the communication channel indicated by the received information.

Preferably, the transmitter may further include a determining unit configured to determine whether or not the predetermined communication channel is available when the communication channel change instruction unit has received the instruction, and the transmitting unit may transmit the information when the predetermined communication channel is determined to be available.

Preferably, the transmitter may further include a notifying unit configured to notify the operator of the fact that it is difficult to change the communication channel when the communication channel indicated by the information is determined not to be available.

Preferably, the receiver may further include a determining unit configured to determine whether or not the communication channel indicated by the information is available based on the received information, and the wireless communication control unit may perform a process of changing the communication channel in use in the wireless communication with the transmitter to the communication channel determined to be available when the communication channel indicated by the information is determined to be available.

Preferably, the wireless communication control unit may prohibit a change of the communication channel in use when the communication channel indicated by the information is determined not to be available.

A wireless image communication apparatus may include: a receiving unit configured to receive image data wirelessly transmitted from an external terminal and receive information regarding a predetermined communication channel designated by an operator from the external terminal during reception of the image data; a determining unit configured to determine whether or not the communication channel indicated by the information is available based on the received information; and a wireless communication control unit configured to perform a process of changing a communication channel in use in wireless communication with the external terminal to the communication channel determined to be available when the communication channel indicated by the information is determined to be available.

Preferably, the wireless image communication apparatus may further include: a transmitting unit configured to transmit determination result information indicating a result of the determination by the determining unit to the external terminal.

According to the present invention, it is possible to change a communication channel in use to a communication channel designated by an operator.

BRIEF DESCRIPTION OF THE DRAWINGS

FIG. 12 is a reference diagram illustrating content of a communication channel setting table in accordance with the first preferred embodiment of the present invention.

FIG. 13 is a reference diagram illustrating content of a scan table in accordance with the first preferred embodiment of the present invention.

FIG. 14 is a reference diagram illustrating a frequency band to be used by a communication channel.

FIG. 15 is a reference diagram illustrating a frequency band to be used by a communication channel.

DESCRIPTION OF THE PREFERRED EMBODIMENTS

Figure 1:
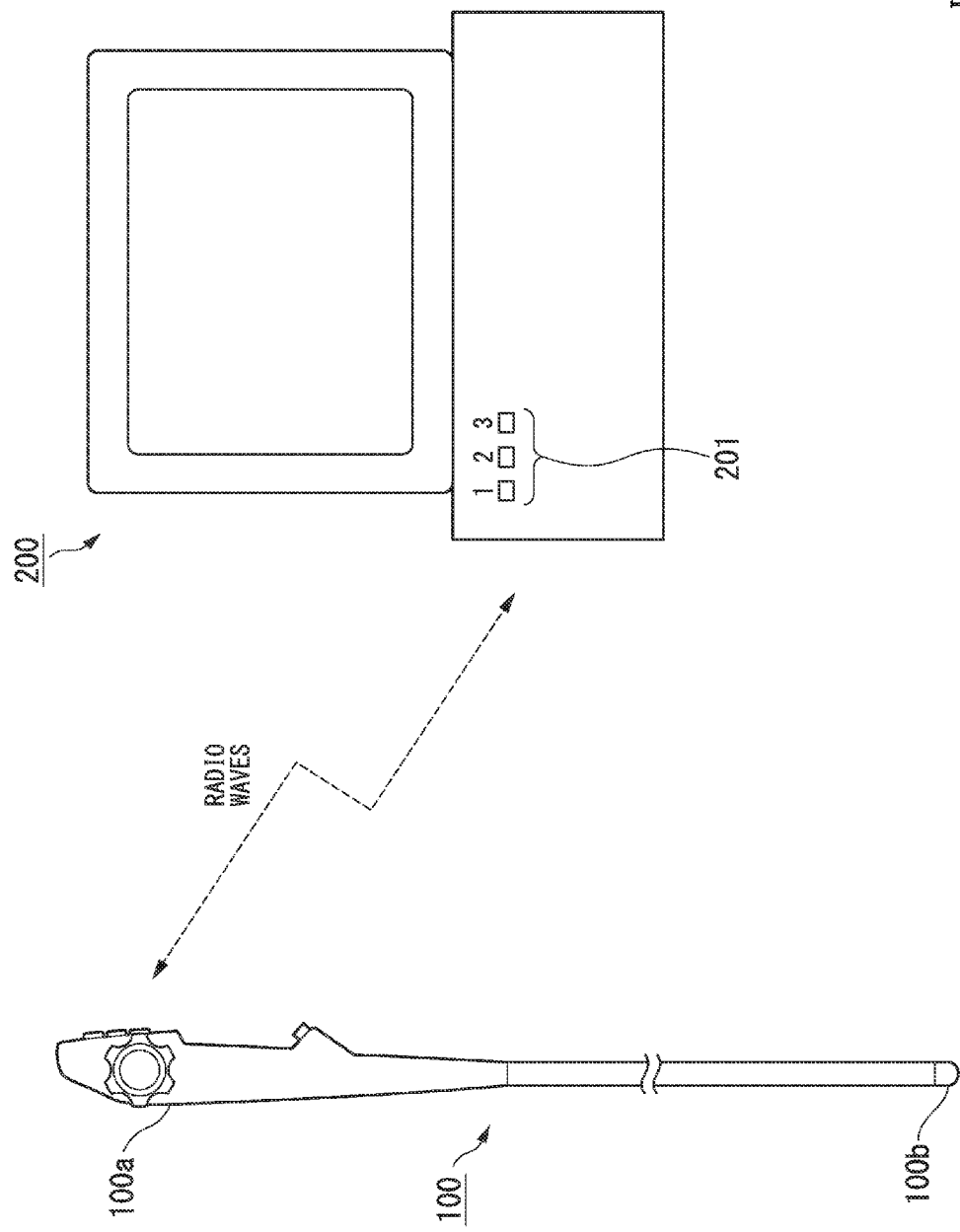
FIG. 1 is a configuration diagram illustrating a configuration of an endoscopic apparatus in accordance with a first preferred embodiment of the present invention.
Figure 2:
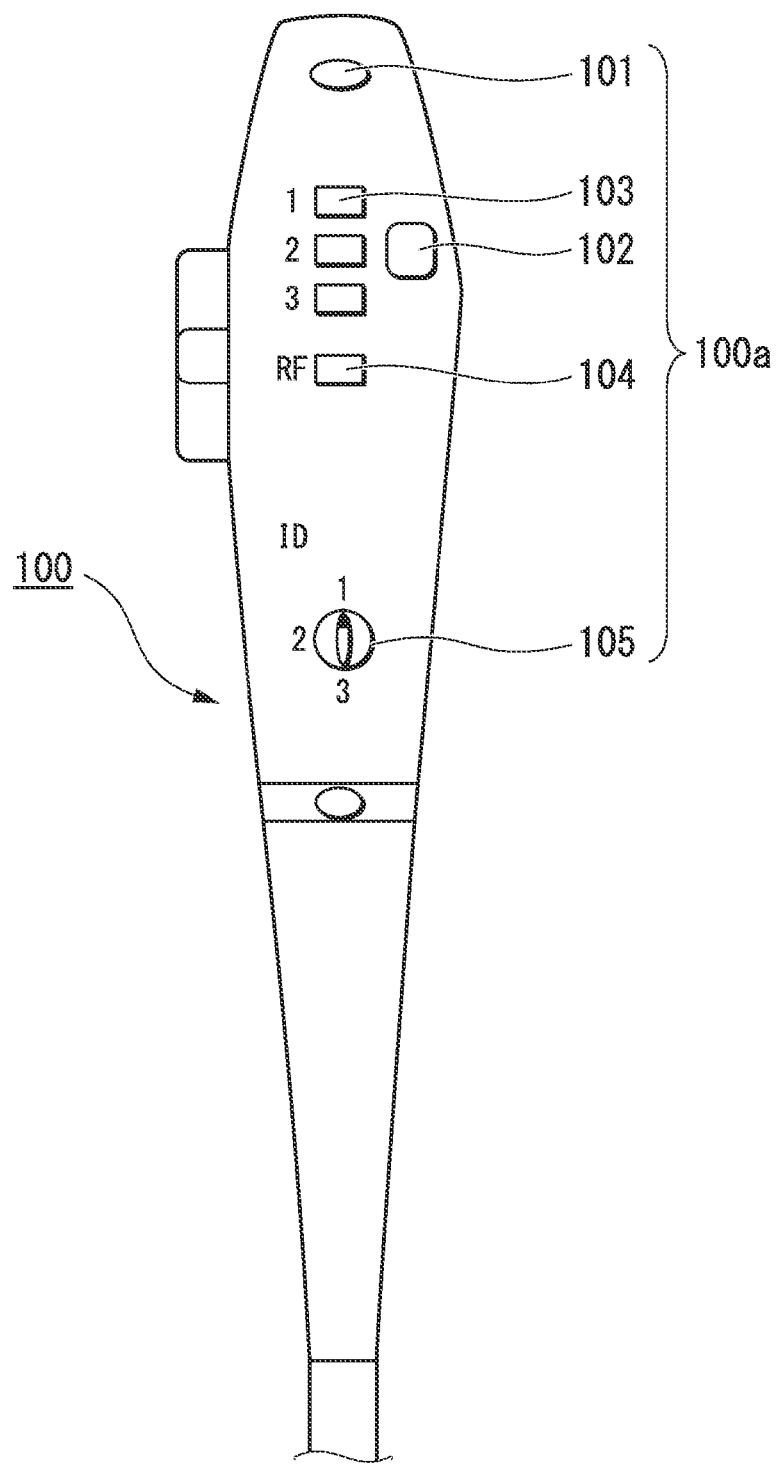
FIG. 2 is an external appearance diagram of an endoscope in accordance with the first preferred embodiment of the present invention.

Hereinafter, preferred embodiments of the present invention will be described with reference to the drawings. FIG. 1 illustrates a configuration of an endoscopic apparatus (wireless image communication system) in accordance with a first preferred embodiment of the present invention. The endoscopic apparatus includes an endoscope 100 (a transmitter: image transmitting apparatus), which transmits captured image data according to wireless communication, and a receiving apparatus 200 (a receiver: image receiving apparatus), which receives the image data transmitted from the endoscope 100 and displays an image on a monitor. The endoscope 100 includes an operation unit 100a including a plurality of switches for allowing an operator to input an operation instruction and a plurality of LEDs. The receiving apparatus 200 includes an identifier (ID) indication unit 201 formed by a plurality of LEDs indicating ID setting states FIG. 2 illustrates a state of the endoscope 100 when viewed from a layout surface of operation switches. An operation unit 100a of the endoscope 100 includes a power-supply switch 101, a communication channel setting switch 102 (a communication channel change instruction unit), a communication channel indication LED 103, a communication state indication LED 104 (a notifying unit), and an ID setting switch 105.

The communication channel setting switch 102 is a switch for allowing the operator to input an instruction to change a communication channel in use in wireless communication with the receiving apparatus 200 to another communication channel. The communication channel is switched every time the operator presses the communication channel setting switch 102 once. The communication channel indication LED 103 includes a plurality of LEDs, and a number is assigned to each LED. In order to notify the operator of a communication channel in use, an LED to which the same number as a number (CH No. to be described later) corresponding to the communication channel in use has been assigned is turned on. The communication state indication LED 104 provides notification of a state of a connection with the receiving apparatus 200.

The ID setting switch 105 is a switch for setting an ID for pairing with the receiving apparatus 200 scheduled to perform communication with the endoscope 100. A plurality of IDs can be provided and an arbitrary ID can be set. Although not illustrated in FIG. 1, it is possible to establish a connection to the receiving apparatus 200 in which the same ID as an ID set in the endoscope 100 is set by providing a switch for setting an ID even on the side of the receiving apparatus 200.

Figure 3:
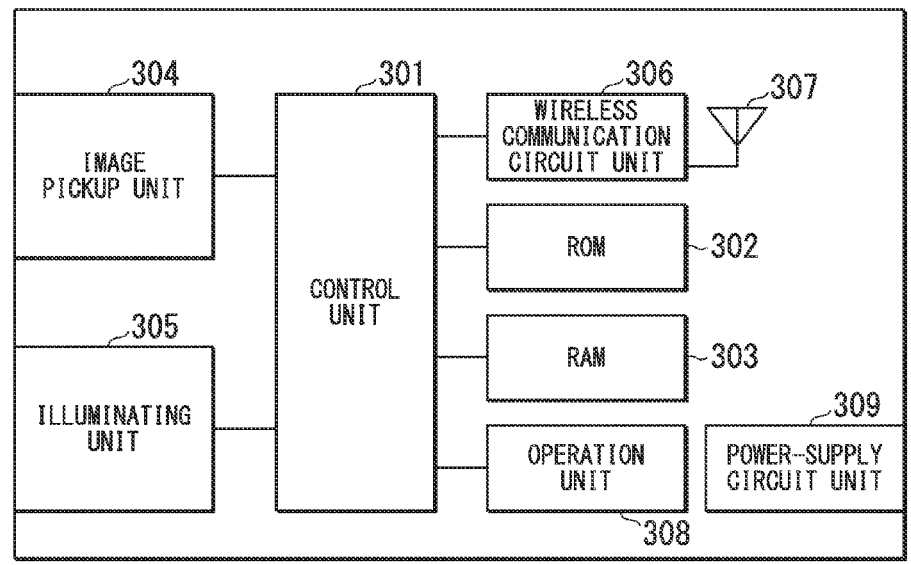
FIG. 3 is a block diagram illustrating a configuration of the endoscope in accordance with the first preferred embodiment of the present invention.

FIG. 3 illustrates an electrical configuration of the endoscope 100. The endoscope 100 includes a control unit 301 (a determining unit), a read only memory (ROM) 302, a random access memory (RAM) 303, an image pickup unit 304, an illuminating unit 305, a wireless communication circuit unit 306 (a transmitting unit), an antenna 307, an operation unit 308, and a power-supply circuit unit 309.

The control unit 301 operates according to a program stored in the ROM 302, and controls an operation sequence of the endoscope 100. The ROM 302 is a non-volatile memory such as a flash ROM. Program data for controlling the endoscope 100, communication setting parameters, and various setting information including a communication channel setting table are stored in the ROM 302. The communication setting parameters include a communication channel (frequency), a service set ID (SSID), wired equivalent privacy (WEP), and the like. The content of a communication channel setting table will be described later.

The RAM 303 is used as a buffer, which temporarily buffers image data output from the image pickup unit 304, a work area for use in an arithmetic operation and the like of the control unit 301, and an area in which various settings and the like are temporarily stored.

The image pickup unit 304 includes a lens, which forms an image of incident light, a photoelectric converter (a charge coupled device (CCD), a complementary metal oxide semiconductor (CMOS) sensor, or the like), which converts light of which an image is formed into an electric signal, an analog-to-digital (AD) converter, which converts an analog electric signal output from the photoelectric converter into a digital electric signal, and the like.

The illuminating unit 305 includes an irradiation lens, an LED, an LED drive circuit, and the like, and is arranged on a tip end 100b (FIG. 1) of the endoscope 100. A body to be observed within a body cavity is irradiated with light emitted from the LED via the irradiation lens. The illuminating unit 305 may have a configuration in which the LED is arranged inside the operation unit 100a, not on the tip end 100b, and light is guided to the tip end 100b by a light guide.

The wireless communication circuit unit 306 includes a high-frequency circuit unit necessary for wireless communication, an encoding/decoding circuit unit, a buffer memory, and the like, and is connected to the antenna 307. In the first preferred embodiment, it is assumed that IEEE 802.11 is used as an example of the wireless communication scheme. To perform wireless communication with the receiving apparatus 200, it is necessary to set the same communication channel, SSID, and the like as those set in the receiving apparatus 200.

The operation unit 308 (corresponding to the operation unit 100a of FIG. 1) includes the power-supply switch 101, the communication channel setting switch 102, the communication channel indication LED 103, the communication state indication LED 104, and the ID setting switch 105 illustrated in FIG. 2, and outputs states and state changes of a button, a switch, and the like, as electric signals.

The power-supply circuit unit 309 includes a battery, a direct current (DC)/DC converter, and the like, and supplies power to each block described above by sensing the turn-on of the power-supply switch 101.

Figure 4:
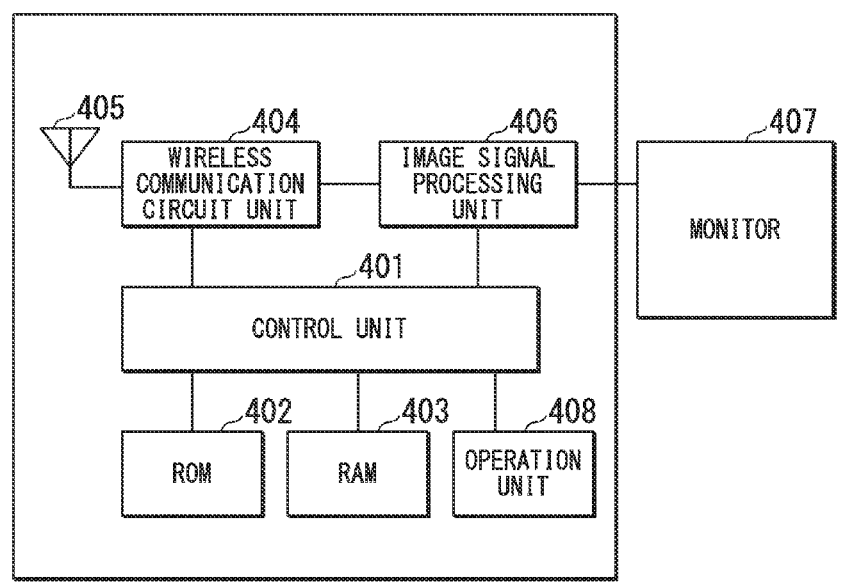
FIG. 4 is a block diagram showing a configuration of a receiving apparatus in accordance with the first preferred embodiment of the present invention.
Figure 5:
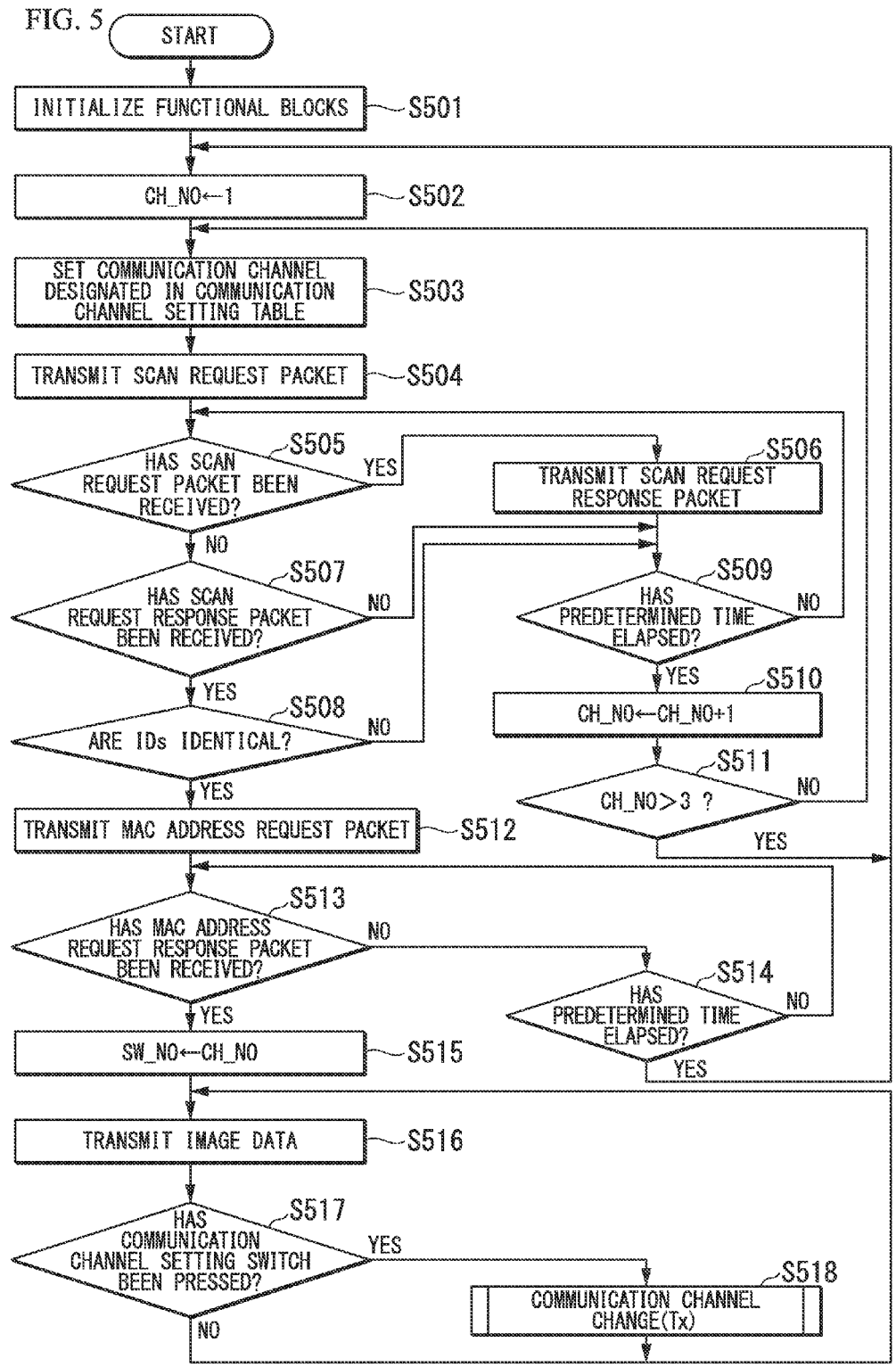
FIG. 5 is a flowchart illustrating an operation of the endoscope in accordance with the first preferred embodiment of the present invention.

FIG. 4 illustrates an electrical configuration of the receiving apparatus 200. The receiving apparatus 200 includes a control unit 401 (a wireless communication control unit and a determining unit), a ROM 402, a RAM 403, a wireless communication circuit unit 404 (a receiving unit and a transmitting unit), an antenna 405, an image signal processing unit 406, a monitor 407, and an operation unit 408.

The control unit 401 operates according to a program stored in the ROM 402, and controls an operation sequence of the receiving apparatus 200. The ROM 402 is a non-volatile memory such as a flash ROM. Program data for controlling the receiving apparatus 200, various setting information including communication setting parameters, a communication channel setting table, and a scan table are stored in the ROM 402. Details of the communication channel setting table and the scan table will be described later.

The RAM 403 is used as a buffer, which temporarily buffers image data received by the wireless communication circuit unit 404, a work area for use in an arithmetic operation and the like of the control unit 401, and an area in which various settings and the like are temporarily stored.

The wireless communication circuit unit 404 includes a high-frequency circuit unit necessary for wireless communication, an encoding/decoding circuit unit, a buffer memory, and the like, and is connected to the antenna 405. Like the wireless communication circuit unit 306 of the endoscope 100, the wireless communication circuit unit 404 performs wireless communication according to the protocol of the wireless LAN.

The image signal processing unit 406 converts image data received by the wireless communication circuit unit 404 into a National Television System Committee (NTSC) signal or a Phase Alternating Line (PAL) signal, and outputs the NTSC or PAL signal to the monitor 407. The monitor 407 includes a liquid crystal display (LCD) apparatus and its control circuit, displays an image, and operates as a notifying unit, which provides notification of a state of a wireless connection.

Although not illustrated in FIG. 1, the operation unit 408 has an ID setting switch mounted on the back of the receiving apparatus 200, and outputs a state and a state change of the ID setting switch as electric signals. In addition, the ID indication unit 201 (FIG. 1), which indicates an ID selected by the ID setting switch using an LED, is arranged in the operation unit 408.

FIG. 12 illustrates content of the communication channel setting table. In the communication channel setting table, a communication channel number is associated with a channel (CH) No. (CH_NO) for identifying a communication channel group. In IEEE 802.11, it is possible to perform wireless communication by selecting an arbitrary communication channel from a plurality of communication channels. Although center frequencies of communication channels are separated by 5 MHz from each other, an overlap of a use frequency band occurs between adjacent communication channels as illustrated in FIG. 15 because each communication channel uses a frequency band of about 20 MHz.

In the first preferred embodiment, thirteen communication channels are provided. Each of the thirteen communication channels belongs to at least one of three communication channel groups corresponding to CH Nos. For example, a communication channel group including communication channels 1, 2, 3, and 4 corresponds to CH No. 1, a communication channel group including communication channels 3, 4, 5, 6, 7, 8, and 9 corresponds to CH No. 2, and a communication channel group including communication channels 8, 9, 10, 11, 12, and 13 corresponds to CH No. 3.

One communication channel of the communication channels belonging to each communication channel group is used in a logical connection to be described later. For example, in a communication channel group corresponding to CH No. 1, communication channel 1 is used in the logical connection. In a communication channel group corresponding to CH No. 2, communication channel 6 is used in the logical connection. In a communication channel group corresponding to CH No. 3, communication channel 11 is used in the logical connection. As illustrated in FIG. 14, frequency bands of the communication channels 1, 6, and 11 do not overlap. One communication channel group includes one communication channel (written as a communication channel in FIG. 12) used in the logical connection and communication channels (written as adjacent channels in FIG. 12) each having a use frequency band partially overlapping that of the one communication channel.

When the above is further generalized, n (n>1) communication channels each having a use frequency band partially overlapping that of at least one other communication channel are provided, and x (1<x≤n) communication channel groups to which L (1≤L<n) communication channels belong are provided In an example shown in the first preferred embodiment, n=13, L=4 (CH No. 1), 7 (CH No. 2), and 6 (CH No. 3), and x=3.

FIG. 13 illustrates content of the scan table. In the scan table, a scan order and a communication channel number belonging to each communication channel are associated with each CH No. Although there is a scan order in which 0 is stored as the communication channel number, 0 is the value used to determine an end of a scan phase to be described later. In the scan phase, the use state of a communication channel is detected in order according to the scan order.

Next, an operation of an endoscopic apparatus in accordance with the first preferred embodiment will be described. In the first preferred embodiment, it is assumed that the endoscope 100 to be used is powered on after the operator has turned on a power supply of the receiving apparatus 200 to be used. Hereinafter, the operation of the endoscope 100 will be described with reference to FIGS. 5 to 8. The operator turns on the power supply of the endoscope 100 after an ID has been set by the ID setting switch 105 of the endoscope 100 according to the ID indicated by the ID indication unit 201 of the receiving apparatus 200. If the endoscope 100 is powered on, the control unit 301 initializes functional blocks of the endoscope 100 (step S501). Subsequently, the control unit 301 initializes a parameter CH_NO indicating a CH No. to 1 (step S502).

Subsequently, the endoscope 100 establishes a physical connection of wireless communication as will be described below. In the physical connection, a radio frequency and an SSID for use in a connection in a physical layer are determined, and a packet that is transmitted/received to/from a communication partner is input to hardware. Specifically, the endoscope 100 transitions to a scan phase of a wireless communication terminal. At the transition to the scan phase, the control unit 301 reads a number of a communication channel (one of communication channels 1, 6, and 11) designated by CH_NO from the communication channel setting table, reads communication setting parameters corresponding to the communication channel of the read number from the ROM 302, and sets the read communication setting parameters in the wireless communication circuit unit 306 (step S503). During an initial operation after power is applied, communication setting parameters corresponding to communication channel 1 are set.

In the scan of the wireless communication terminal, a scan request packet is transmitted, and the reception of a scan request response packet to the scan request packet is performed during a predetermined period. For this, the control unit 301 causes the wireless communication circuit unit 306 to broadcast the scan request packet (step S504).

The control unit 301 determines whether or not the scan request packet has been received from another wireless communication terminal after the transmission of the scan request packet (step S505). When the scan request packet has been received, the control unit 301 causes the wireless communication circuit unit 306 to transmit the scan request response packet to a transmission source of the scan request packet (step S506). The scan request response packet of the first preferred embodiment includes an ID set by the ID setting switch. In addition, when the scan request packet has not been received, the control unit 301 determines whether or not the scan request response packet has been received (step S507).

When the scan request response packet has been received, the control unit 301 compares the ID set by the ID setting switch 105 with an ID included in the scan request response packet, and determines whether or not the two IDs are identical (step S508). As will be described later, the receiving apparatus 200 detects a use state of each communication channel while sequentially changing a communication channel in the scan phase. When the receiving apparatus 200 scheduled to be connected uses the same communication channel as a communication channel set in the endoscope 100, the scan request response packet including the same ID as the ID set by the ID setting switch 105 is received. Therefore, it is possible to check the presence of the receiving apparatus 200 scheduled to be connected by making a determination based on the ID. When the ID set by the ID setting switch 105 is the same as the ID included in the scan request response packet, the process proceeds to step S512.

When the scan request response packet has been transmitted in step S506, when the scan request response packet has not been received in step S507, and when the ID set by the ID setting switch 105 is not the same as the ID included in the scan request response packet in step S508, the control unit 301 determines whether or not a predetermined time has elapsed after the scan request packet was transmitted in step S504 (step S509). When the predetermined time has not elapsed, the process returns to the step S505. In addition, when the predetermined time has elapsed, the control unit 301 adds 1 to a value of CH_NO and updates the value (step S510).

Subsequently, the control unit 301 determines whether or not the value of CH_NO exceeds 3 (step S511). When the value of CH_NO exceeds 3, the process returns to step S502. In addition, when the value of CH_NO does not exceed 3, the process returns to step S503.

On the other hand, when the ID set by the ID setting switch 105 is the same as the ID included in the scan request response packet in step S508, the endoscope 100 transitions to a logical connection phase. To establish the logical connection, the control unit 301 causes the wireless communication circuit unit 306 to transmit a media access control (MAC) address request packet to the receiving apparatus 200 (step S512). After the transmission of the MAC address request packet, the control unit 301 determines whether or not a MAC address request response packet has been received from the receiving apparatus 200 (step S513).

As will be described later, the receiving apparatus 200 selects a communication channel that is unlikely to cause radio-wave interference with communication channels used by peripheral wireless communication terminals as a communication channel for use in communication of image data with the endoscope 100. After the above-described communication channel has been selected, the receiving apparatus 200 returns a MAC address request response packet when the MAC address request packet has been received. When the same communication channel is set in the endoscope 100 and the receiving apparatus 200, the MAC address request response packet from the receiving apparatus 200 is received by the endoscope 100.

When the MAC address response packet has been received, the logical connection is completed. A MAC address is exchanged between the endoscope 100 and the receiving apparatus 200 according to transmission/reception of the MAC address request packet and the MAC address request response packet. When the logical connection is established, a combination of two specific wireless communication terminals, that is, the endoscope 100 and the receiving apparatus 200, among a plurality of physically connected communication terminals is established, and a destination (MAC address) of the image data to be transmitted by the endoscope 100 is established.

Subsequently, the control unit 301 sets a value of a parameter SW_NO indicating a CH No. corresponding to a communication channel to be set by the operator to the same value as a value of CH_NO (step S515). Subsequently, the wireless communication circuit unit 306 transmits the image data to the receiving apparatus 200 (step S516). In step S516, an arbitrary amount of image data such as image data for one screen or image data for one of blocks into which one screen is divided is transmitted. Subsequently, the control unit 301 determines whether or not the operator has pressed the communication channel setting switch 102 (step S517).

When the communication channel setting switch 102 has been pressed, the control unit 301 performs a communication channel change process for changing a communication channel in use to another communication channel (step S518). After the communication channel change process, the process returns to step S516, and the next image data is transmitted.

On the other hand, when the communication channel setting switch 102 is not pressed in step S517, the process returns to step S516 and the next image data is transmitted.

Figure 6:
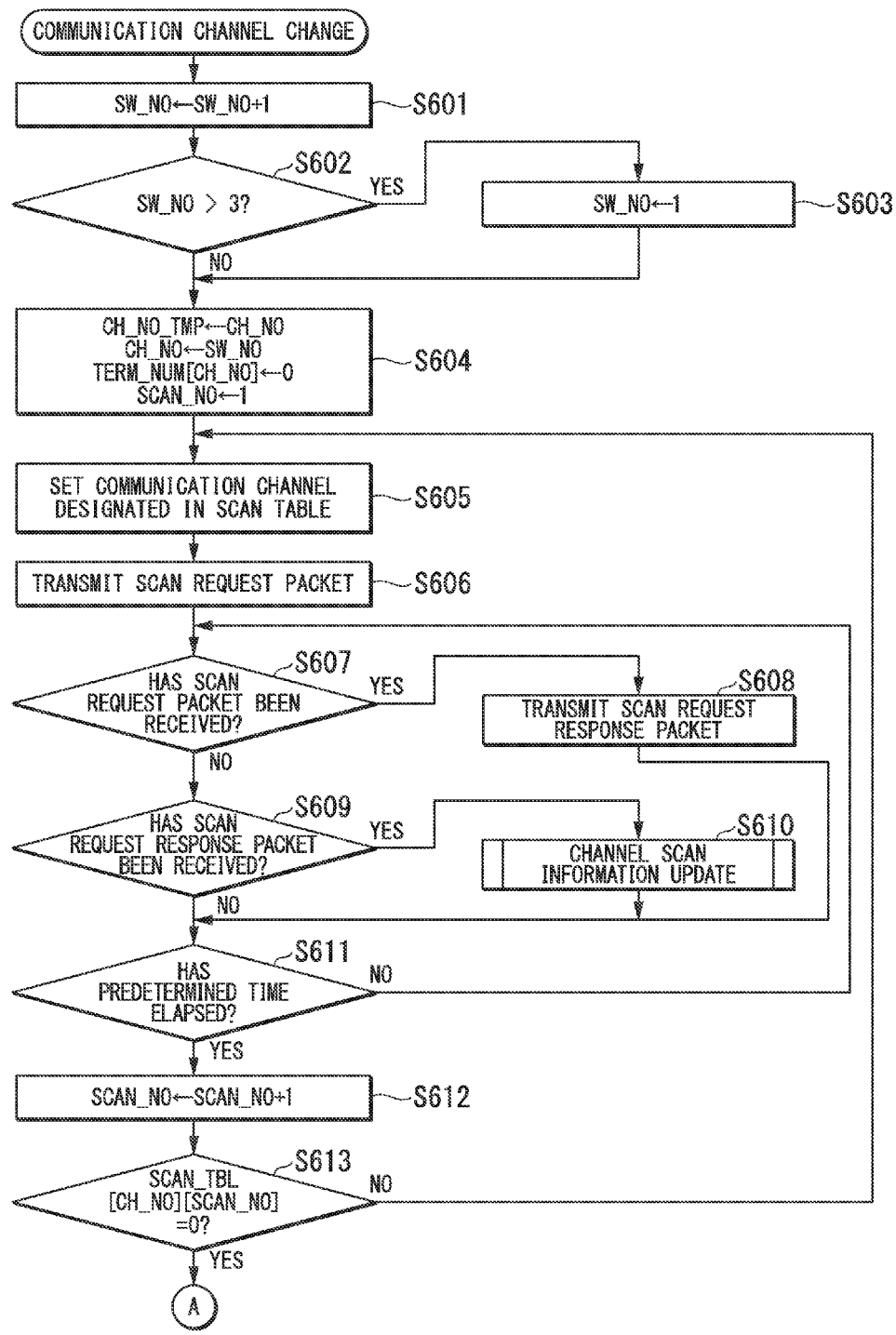
FIG. 6 is a flowchart illustrating an operation of the endoscope in accordance with the first preferred embodiment of the present invention.
Figure 7:
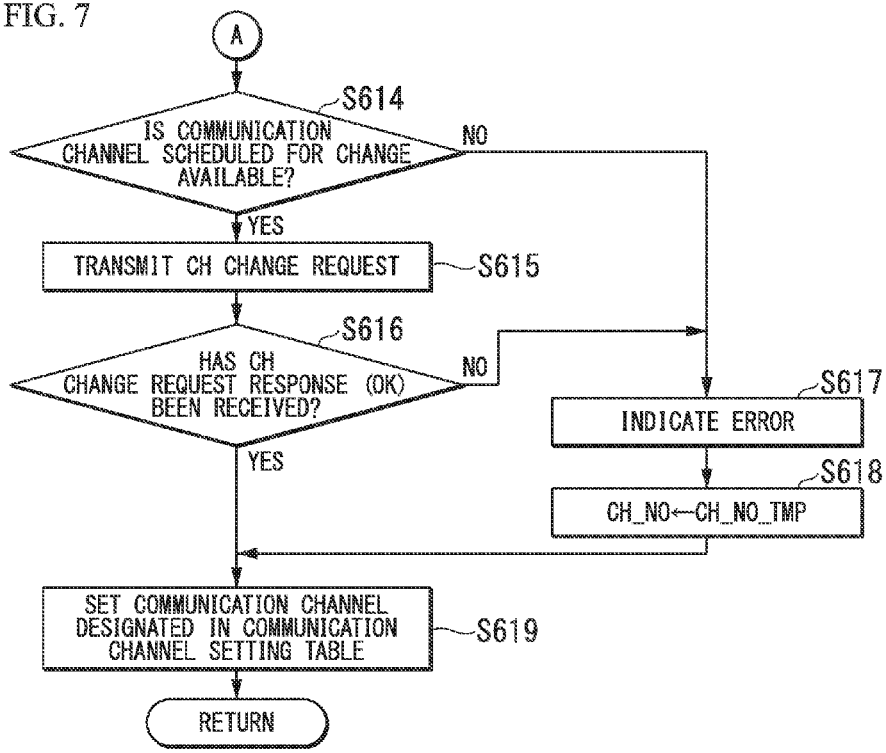
FIG. 7 is a flowchart illustrating an operation of the endoscope in accordance with the first preferred embodiment of the present invention.

FIGS. 6 and 7 illustrate details of the communication channel change process in step S518. As will be described below, in step S518, after a process of checking whether or not a communication channel to be set by the operator is available has been performed, a communication channel is changed when the communication channel is available.

After the endoscope 100 has been powered on, a CH No. corresponding to a communication channel when the endoscope 100 has been initially connected to the receiving apparatus 200 is set as an initial value of SW_NO in step S515. As will be described later, because the receiving apparatus 200 waits for a communication channel having the best communication environment to be set and connected after the application of power, the initial value of SW_NO at the initiation of step S518 indicates the communication channel having the best communication environment.

First, the control unit 301 adds 1 to the value of SW_NO, and updates the value (step S601). Subsequently, the control unit 301 determines whether or not the value of SW_NO exceeds 3 (step S602). When the value of SW_NO does not exceed 3, the process proceeds to step S604. In addition, when the value of SW_NO exceeds 3, the control unit 301 initializes the value of SW_NO to 1 (step S603).

Subsequently, the control unit 301 sets values for parameters CH_NO_TMP, CH_NO, TERM_NUM[CH_NO], and SCAN_NO for use in subsequent control (step S604). CH_NO_TMP is a parameter for temporarily holding the value of CH_NO, and the same value as the value of CH_NO is set to a value of CH_NO_TMP. CH_NO is a parameter indicating a CH No. as described above, and the same value as the value of the parameter SW_NO indicating a CH No. corresponding to a communication channel to be set by the operator is set to the value of CH_NO. TERM_NUM [CH_NO] is a parameter for storing the number of peripheral wireless communication terminals using a communication channel satisfying a predetermined condition, and its value is set to 0,SCAN_NO is a parameter for storing a scan order in the scan table, and its value is set to 1.

Subsequently, the endoscope 100 transitions to a communication channel scan phase. At the time of the transition to the scan phase, the control unit 301 reads a number of a communication channel (a communication channel in which a CH No. is CH_NO and a scan order is SCAN_NO) designated by CH_NO and SCAN_NO from the scan table, reads communication setting parameters corresponding to the communication channel from the ROM 302, and sets the read communication setting parameters in the wireless communication circuit unit 306 (step S605). In the communication channel scan, a scan request packet is transmitted, and the reception of a scan request response packet to the scan request packet is performed during a predetermined period. For this, the control unit 301 causes the wireless communication circuit unit 306 to broadcast the scan request packet (step S606). A wireless communication terminal in which the same communication channel as that of the endoscope 100 is set receives the scan request packet transmitted from the endoscope 100 and transmits the scan request response packet.

After the transmission of the scan request packet, the control unit 301 determines whether or not the scan request packet has been received from another wireless communication terminal (step S607). When the scan request packet has been received, the control unit 301 causes the wireless communication circuit unit 306 to transmit the scan request response packet to a transmission source of the scan request packet (step S608). As described above, the scan request response packet includes an ID designated by the ID setting switch. Thereafter, the process proceeds to step S611. In addition, when the scan request packet has not been received, the control unit 301 determines whether or not the scan request response packet has been received from another wireless communication terminal (step S609). When the scan request response packet has been received, the control unit 301 executes a process of updating a value of TERM_NUM[CH_NO] (channel scan information) (step S610). Thereafter, the process proceeds to step S611. In addition, when the scan request response packet has not been received, the process proceeds to step S611.

Figure 8:
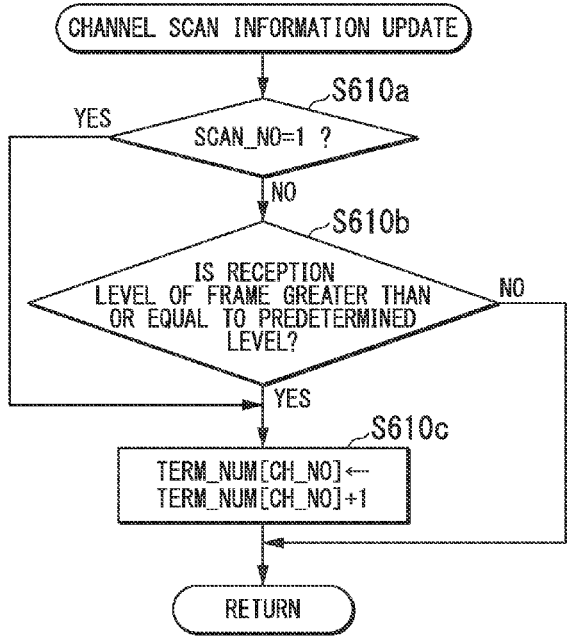
FIG. 8 is a flowchart illustrating an operation of the endoscope in accordance with the first preferred embodiment of the present invention.

FIG. 8 illustrates details of step S610. The control unit 301 determines whether or not the value of SCAN_NO is 1 (step S610a). When the value of SCAN_NO is 1, the process proceeds to step S610c. In addition, when the value of SCAN_NO is not 1, the control unit 301 determines whether or not a reception level (received signal strength) of a frame of the scan request response packet is greater than or equal to a predetermined level (step S610b). When the reception level of the frame is greater than or equal to the predetermined level, the process proceeds to step S610c. In addition, when the reception level of the frame is less than the predetermined level, the process proceeds to step S611. When the process proceeds to step S610c, the control unit 301 adds 1 to the value of TERM_NUM[CH_NO], and updates the value (step S610c). After the process of step S610c, the process proceeds to step S611.

The value of TERM_NUM[CH_NO] indicates the number of peripheral wireless communication terminals using the same communication channel as one of communication channels 1, 6, and 11 or using a communication channel of which a use frequency band overlaps that of one of communication channels 1, 6, and 11. When the value of SCAN_NO is 1 in step S610a, another wireless communication terminal uses the same communication channel as one of communication channels 1, 6, and 11. In addition, when the reception level of the frame is greater than or equal to the predetermined level in step S610b, another wireless communication terminal uses a communication channel of which a use frequency band overlaps that of one of communication channels 1, 6, and 11. In the first preferred embodiment, although a common threshold value is set as a threshold value of the reception level of the frame in each adjacent channel, a predetermined threshold value of the reception level may be set for every adjacent channel.

When the process has proceeded to step S611, the control unit 301 determines whether or not a predetermined time has elapsed after the scan request packet was transmitted in step S606 (step S611). When the predetermined time has not elapsed, the process returns to step S607. In addition, when the predetermined time has elapsed, the control unit 301 adds 1 to the value of SCAN_NO and updates the value (step S612).

Subsequently, the control unit 301 reads a number of a communication channel (a communication channel in which a CH No. is CH_NO and a scan order is SCAN_NO) designated by CH_NO and SCAN_NO after the update from the scan table, and determines whether or not the number is 0 (step S613). When the number of the communication channel designated by CH_NO and SCAN_NO after the update is not 0, the process returns to step S605.

When the number of the communication channel designated by CH_NO and SCAN_NO after the update is 0, the control unit 301 determines whether or not a communication channel (one of communication channels 1, 6, and 11) scheduled for a change designated by a CH No. is available (step S614). In the first preferred embodiment, when the number of wireless terminals, TERM_NUM[CH_NO], counted in step S610 of FIG. 8 is less than a predetermined threshold value, the control unit 301 determines that the communication channel is available.

When the communication channel is determined to be available, the control unit 301 causes the wireless communication circuit unit 306 to transmit a CH change request to the currently connected receiving apparatus 200 (step S615). This CH change request includes the value of CH_NO indicating a CH No. of the communication channel determined to be available. According to the transmission of the CH change request, information regarding a communication channel to be set by the operator is transmitted to the currently connected receiving apparatus 200.

Subsequently, the control unit 301 determines whether or not a CH change request response indicating that the change of the communication channel is possible (OK) has been received (step S616). When the CH change request response indicating that the change of the communication channel is possible (OK) has been received, it is checked that the communication channel to be set by the user is available in both the endoscope 100 and the receiving apparatus 200. In this case, the control unit 301 reads a number of a communication channel (one of communication channels 1, 6, and 11) designated by CH_NO from the communication channel setting table, reads communication setting parameters corresponding to the communication channel of the number from the ROM 302, and sets the read communication setting parameters in the wireless communication circuit unit 306 (step S619). Subsequently, the process returns to step S516. Thereby, the communication channel designated by the user according to an operation of the communication channel setting switch 102 is set, and communication of image data is performed.

When the communication channel is determined not to be available in step S614 and the CH change request response indicating that the change of the communication channel is possible (OK) has not been received in step S616, the control unit 301 sets a state of the communication state indication LED 104 to an error indication state. Thereby, the operator is notified of the fact that it is difficult to change the communication channel.

Subsequently, the control unit 301 sets the value of CH_NO to the same value as the value of CH_NO_TMP (step S618). Subsequently, the process proceeds to step S619, and communication setting parameters corresponding to a communication channel designated by CH_NO are set in the wireless communication circuit unit 306. That is, the communication channel is not changed, and the same communication channel as the communication channel set in step S503 is continuously set. As described above, when the communication channel to be set by the operator is not available, the change to the communication channel is set to be prohibited.

Figure 9:
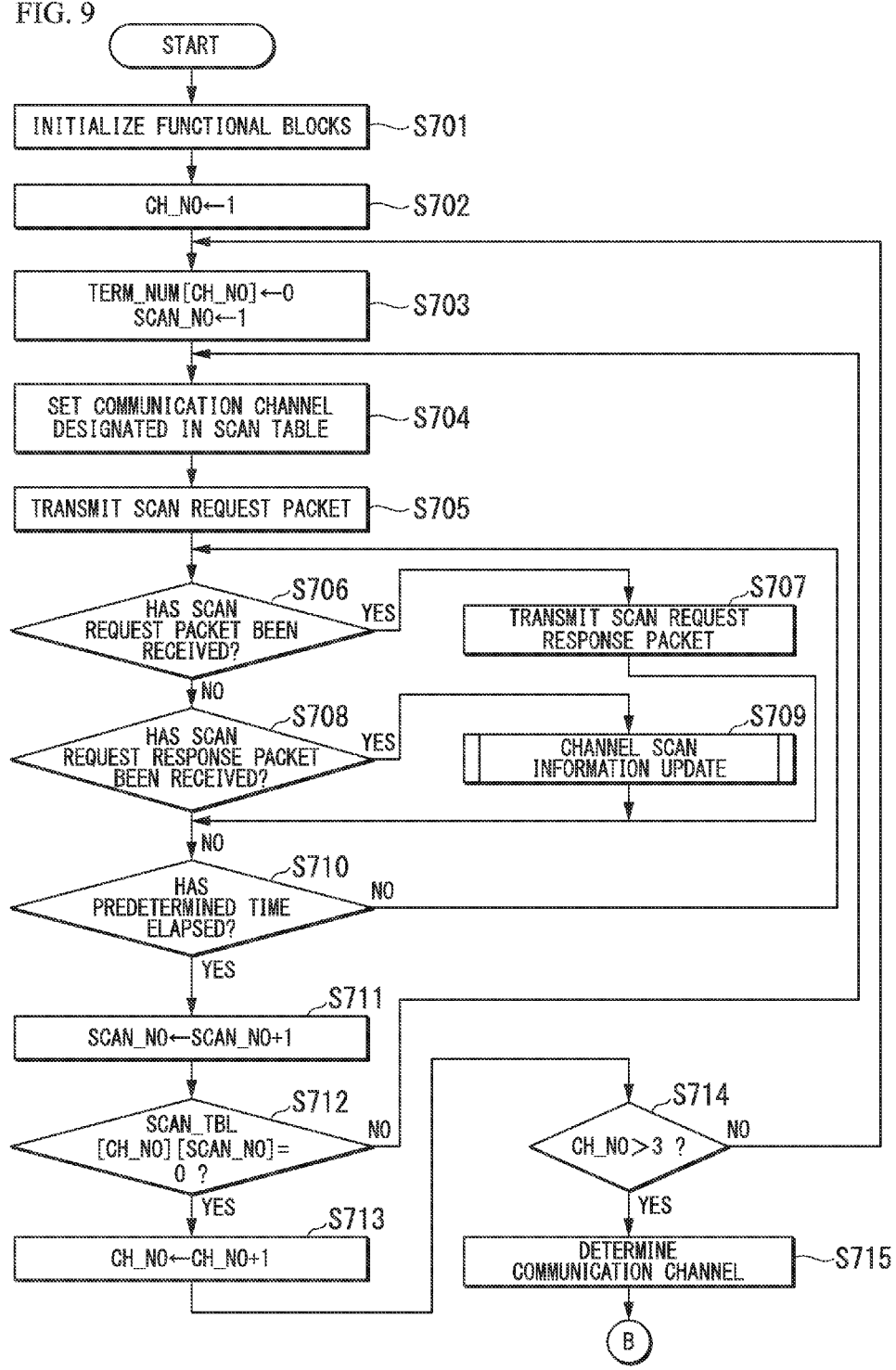
FIG. 9 is a flowchart illustrating an operation of the receiving apparatus in accordance with the first preferred embodiment of the present invention.
Figure 10:
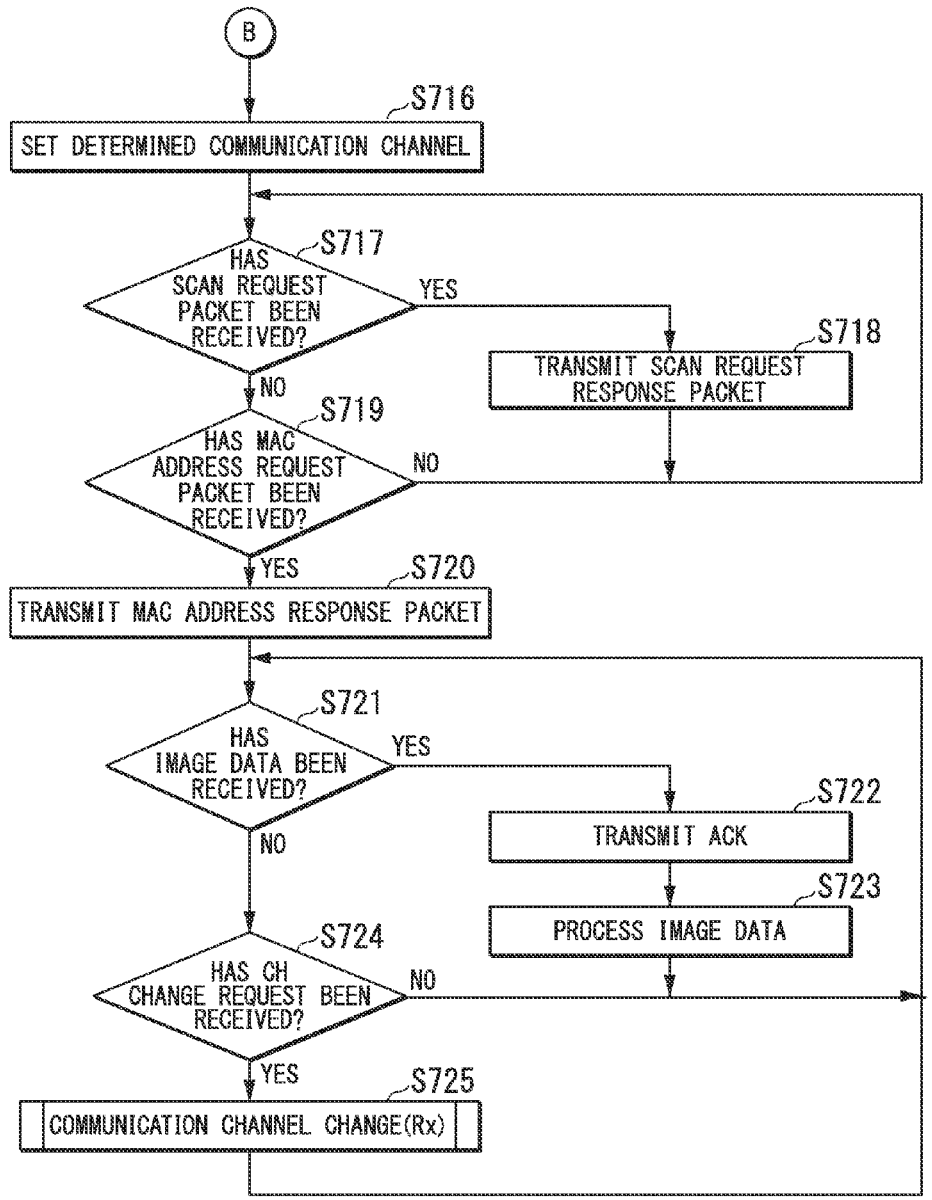
FIG. 10 is a flowchart illustrating an operation of the receiving apparatus in accordance with the first preferred embodiment of the present invention.

Next, an operation of the receiving apparatus 200 will be described with reference to FIGS. 9 and 10. After the operator has set an ID according to the ID setting switch of the receiving apparatus 200, the receiving apparatus 200 is powered on. When the receiving apparatus 200 is powered on, the control unit 401 initializes functional blocks of the receiving apparatus 200 (step S701).

Subsequently, the control unit 401 initializes the parameter CH_NO for use in subsequent control (step S702), and then initializes the parameters TERM_NUM[ ] and SCAN_NO (step S703). CH_NO is a parameter indicating a CH No. as described above, and the value of CH_NO is set to 1 at the time of initialization. TERM_NUM[CH_NO] is a parameter for storing the number of peripheral wireless communication terminals using a communication channel satisfying a predetermined condition, and its value is set to 0.

Subsequently, the receiving apparatus 200 establishes a physical connection of wireless communication. Specifically, the receiving apparatus 200 transitions to a communication channel scan phase. At the time of the transition to the scan phase, the control unit 401 reads a number of a communication channel (a communication channel in which a CH No. is CH_NO and a scan order is SCAN_NO) designated by CH_NO and SCAN_NO from the scan table, reads communication setting parameters corresponding to the communication channel from the ROM 402, and sets the read communication setting parameters in the wireless communication circuit unit 404 (step S704). In the communication channel scan, a scan request packet is transmitted, and the reception of a scan request response packet to the scan request packet is performed during a predetermined period. For this, the control unit 401 causes the wireless communication circuit unit 404 to broadcast the scan request packet (step S705). A wireless communication terminal in which the same communication channel as that of the receiving apparatus 200 is set receives the scan request packet transmitted from the receiving apparatus 200 and transmits a scan request response packet.

After the transmission of the scan request packet, the control unit 401 determines whether or not the scan request packet has been received from another wireless communication terminal (step S706). When the scan request packet has been received, the control unit 401 causes the wireless communication circuit unit 404 to transmit the scan request response packet to a transmission source of the scan request packet (step S707). As described above, the scan request response packet includes an ID designated by the ID setting switch. Thereafter, the process proceeds to step S710. In addition, when the scan request packet has not been received, the control unit 401 determines whether or not the scan request response packet has been received from another wireless communication terminal (step S708). When the scan request response packet has been received, the control unit 401 executes a process of updating the value of TERM_NUM [CH_NO] (channel scan information) (step S709). Thereafter, the process proceeds to step S710. In addition, when the scan request response packet has not been received, the process proceeds to step S710.

Because the process of step S709 is substantially the same as the process illustrated in FIG. 8, description thereof is omitted. When the process has proceeded to step S710, the control unit 401 determines whether or not a predetermined time has elapsed after the scan request packet was transmitted in step S705 (step S710). When the predetermined time has not elapsed, the process returns to step S706. In addition, when the predetermined time has elapsed, the control unit 401 adds 1 to the value of SCAN_NO and updates the value (step S711).

Subsequently, the control unit 401 reads a number of a communication channel (a communication channel in which a CH No. is CH_NO and a scan order is SCAN_NO) designated by CH_NO and SCAN_NO after the update from the scan table, and determines whether or not the number is 0 (step S712). When the number of the communication channel designated by CH_NO and SCAN_NO after the update is not 0, the process returns to step S704. In addition, when the number of the communication channel designated by CH_NO and SCAN_NO after the update is 0, the control unit 401 adds 1 to the value of CH_NO and updates the value (step S713).

Subsequently, the control unit 401 determines whether or not the value of CH_NO exceeds 3 (step S714). When the value of CH_NO does not exceed 3, the process returns to step S703. In addition, when the value of CH_NO exceeds 3, the control unit 401 determines a communication channel to be used based on a value of TERM_NUM[CH_NO]. Specifically, the control unit 401 compares the number of wireless communication terminals, TERM_NUM[1], TERM_NUM [2], and TERM_NUM[3], counted in step S709, and determines a communication channel corresponding to the smallest number of wireless communication terminals as a communication channel for use in the logical connection (step S715).

Specifically, when TERM_NUM[1] is smallest, communication channel 1 corresponding to CH No. 1 is selected. When TERM_NUM[2] is smallest, communication channel 6 corresponding to CH No. 2 is selected. When TERM_NUM [3] is smallest, communication channel 11 corresponding to CH No. 3 is selected. As described above, it is possible to select a communication channel having the best communication state using a communication channel corresponding to a smallest value of TERM_NUM[CH_NO] (CH_NO=1, 2, 3). After the determination of the communication channel, the control unit 401 reads communication setting parameters corresponding to the determined communication channel from the ROM 402, and sets the read communication setting parameters in the wireless communication circuit unit 404 (step S716).

Subsequently, the receiving apparatus 200 transitions to a logical connection phase. The control unit 401 determines whether or not the scan request packet has been received from another wireless communication terminal (step S717). When the scan request packet has been received, the control unit 401 causes the wireless communication circuit unit 404 to transmit a scan request response packet to a transmission source of the scan request packet (step S718). Thereafter, the process returns to step S717. In addition, when the scan request packet has not been received, the control unit 401 determines whether or not a MAC address request packet has been received from the endoscope 100 (step S719).

When the MAC address request packet has not been received, the process returns to step S717. In addition, when the MAC address request packet has been received, the control unit 401 causes the wireless communication circuit unit 404 to transmit a MAC address request response to the endoscope 100 (step S720). Subsequently, the control unit 401 determines whether or not image data has been received (step S721). When the image data has been received, the wireless communication circuit unit 404 notifies the control unit 401 of the reception of the image data.

When the image data has been received, the control unit 401 causes the wireless communication circuit unit 404 to transmit an acknowledgement (ACK) to the endoscope 100 (step S722). After the transmission of the ACK, the image signal processing unit 406 processes the received image data and outputs the processed image data to the monitor 407. The monitor 407 displays an image based on the image data (step S723). Subsequently, the process returns to step S721.

On the other hand, when the image data has not been received, the control unit 401 determines whether or not a CH change request has been received from the endoscope 100 (step S724). When the CH change request has been received, the control unit 401 performs a communication channel change process for changing a communication channel in use to another communication channel based on the CH change request (step S725). Subsequently, the process returns to step S721. In addition, when the CH change request has not been received, the process returns to step S721.

Figure 11:
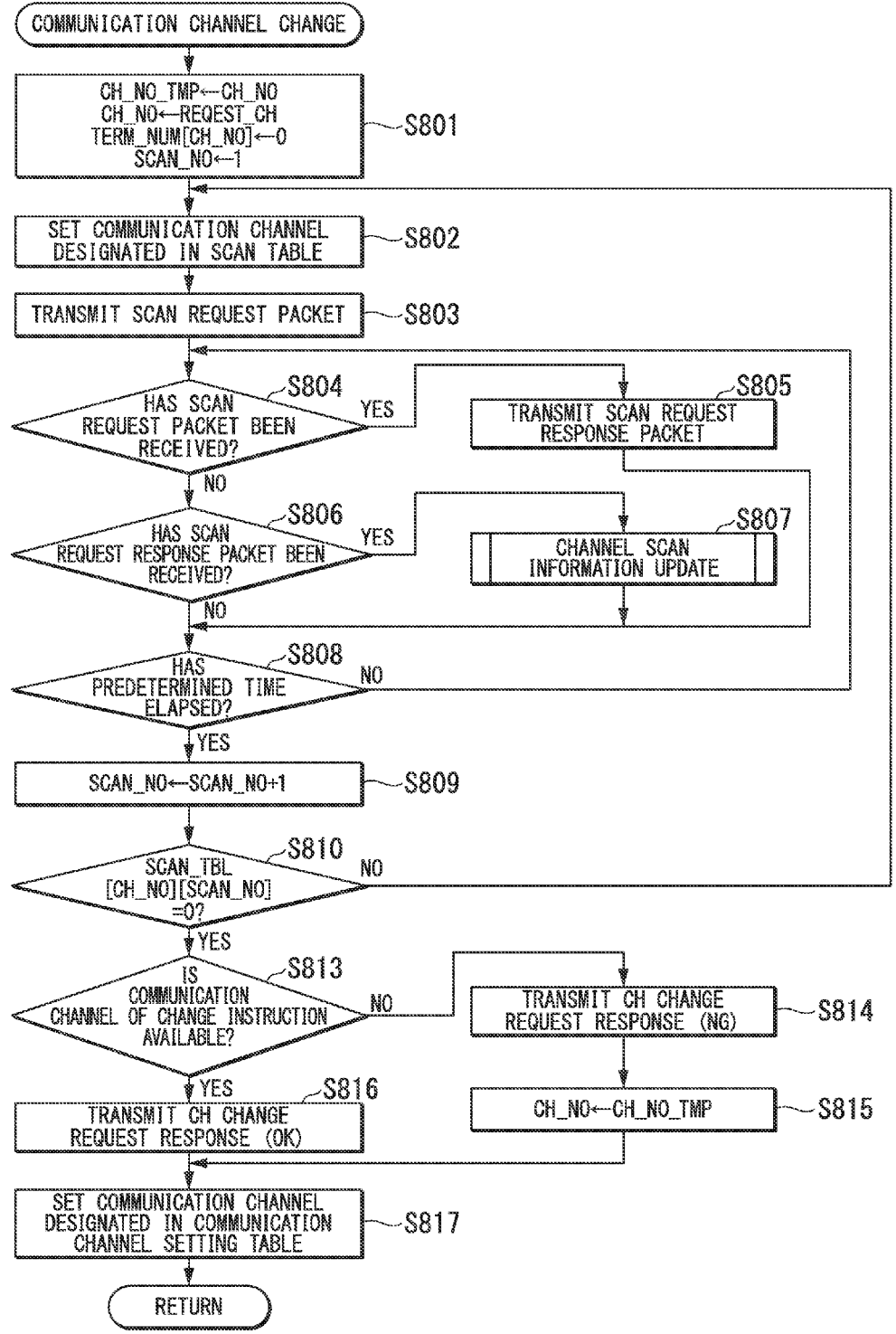
FIG. 11 is a flowchart illustrating an operation of the receiving apparatus in accordance with the first preferred embodiment of the present invention.

FIG. 11 illustrates details of step S725. The control unit 401 initializes parameters CH_NO_TMP, CH_NO, TERM_NUM[CH_NO], and SCAN_NO for use in subsequent control (step S801). CH_NO_TMP is a parameter for temporarily holding the value of CH_NO, and the same value as the value of CH_NO is set to a value of CH_NO_TMP. CH_NO is a parameter indicating a CH No. as described above, and the same value as the value of CH_NO included in the CH change request is set to the value of CH_NO. TERM_NUM[CH_NO] is a parameter for storing the number of peripheral wireless communication terminals using a communication channel satisfying a predetermined condition, and its value is set to 0, SCAN_NO is a parameter for storing a scan order in the scan table, and its value is set to 1.

Because the process of steps S802 to S810 to be performed subsequent to the process of step S801 is the same as the process of steps S704 to S712, description thereof is omitted. When a number of a communication channel designated by CH_NO and SCAN_NO after update is 0 in step S810, the control unit 401 determines whether or not a communication channel (one of communication channels 1, 6, and 11) corresponding to a CH No. (CH_NO) indicated by the CH change request is available (step S813). In the first preferred embodiment, when the number of wireless terminals, TERM_NUM [CH_NO], counted in step S807 is less than a predetermined threshold value, the control unit 401 determines that the communication channel is available.

When the communication channel is determined to be available, the control unit 401 causes the wireless communication circuit unit 404 to transmit a CH change request response indicating that the change of the communication channel is possible to the currently connected endoscope 100 (step S816). Subsequently, the control unit 401 reads a number of a communication channel (one of communication channels 1, 6, and 11) designated by CH_NO from the communication channel setting table, reads communication setting parameters corresponding to the communication channel of the read number from the ROM 402, and sets the read communication setting parameters in the wireless communication circuit unit 404 (step S817). Subsequently, the process returns to step S721. Thereby, a communication channel designated by the user according to an operation of the communication channel setting switch 102 is set, and communication of image data is performed.

When the communication channel is determined not to be available in step S813, the control unit 401 causes the wireless communication circuit unit 404 to transmit a CH change request response indicating that it is difficult to change the communication channel to the currently connected endoscope 100 (step S814). Subsequently, the control unit 401 sets the value of CH_NO to the same value as a value of CH_NO_TMP (step S815). Subsequently, the process proceeds to step S817, and communication setting parameters corresponding to a communication channel designated by CH_NO are set in the wireless communication circuit unit 404. That is, the communication channel is not changed, and the setting of the same communication channel as the communication channel set in step S802 is continued. As described above, when the communication channel to be set by the operator is not available, the change to the communication channel is prohibited.

In the above-described operation, during an initial operation, the control unit 401 selects a communication channel group designated by a CH No. (CH_NO) (step S704). In addition, the control unit 401 detects the number of peripheral wireless communication terminals using the same communication channel as one of communication channels 1, 6, and 11 belonging to the communication channel group or using a communication channel of which a use frequency band overlaps that of one of communication channels 1, 6, and 11 as a communication channel use state (steps S705 to S714). Further, the control unit 401 determines the communication channel for use in a logical connection based on the detection result of the communication channel use state (step S715).

As described above, it is possible to efficiently select a communication channel having the best communication state during an initial operation by detecting use states of only communication channels belonging to a communication channel group. In addition, in step S715, it is possible to reduce the occurrence of a communication error by selecting a communication channel that is unlikely to cause radio-wave interference with communication channels used by peripheral wireless communication terminals.

As described above, in accordance with the first preferred embodiment, the endoscope 100 and the receiving apparatus 200 can change a communication channel for use in wireless communication to a communication channel designated by the operator.

In addition, the endoscope 100 and the receiving apparatus 200 can prevent the contention of a radio band with another wireless communication apparatus by checking a use state of a communication channel scheduled for a change. Although a process of checking a use state of a communication channel scheduled for the change may be checked by only one of the endoscope 100 and the receiving apparatus 200, it is more desirable to perform the process in both the endoscope 100 and the receiving apparatus 200 because there is a difference between use states of communication channels due to a difference between positions of the endoscope 100 and the receiving apparatus 200.

In addition, when the communication channel scheduled for the change is determined not to be available, it is possible to prevent the contention of a radio band with another wireless communication apparatus by prohibiting a change of the communication channel in use.

In addition, when the communication channel is determined not to be available, it is possible to prompt the operator to make a change to another communication channel by notifying the operator of the fact that it is difficult to change the communication channel.

While preferred embodiments of the present invention have been described and illustrated above, it should be understood that these are examples of the present invention and are not to be considered as limiting. Additions, omissions, substitutions, and other modifications can be made without departing from the scope of the present invention.

The present invention can be widely applied to a wireless image communication system and a wireless image communication apparatus that transmit/receive image data through wireless communication using a wireless communication scheme such as a wireless LAN.

What is claimed is:

1. A wireless image communication system for an endoscope apparatus, comprising a transmitter that wirelessly transmits image data and a receiver that receives the image data transmitted from the transmitter, wherein the transmitter comprises:
a channel setting switch configured to set a communication channel, which is used in wireless communication with the receiver related to transmission of the image data; and
a transmitter communication unit configured to wirelessly transmit the image data to the receiver, and the receiver comprises:
a receiver communication unit configured to receive the image data wirelessly transmitted from the transmitter, when a second communication channel, which is different from a first communication channel that has been set, is newly set, then
at least one of the transmitter and the receiver includes a determination unit configured to perform a detection of a use state of each of the second communication channel and adjacent communication channels and to determine whether or not the second communication channel is available based on a result of the detection,
the transmitter and the receiver perform a process of changing the communication channel to use in the wireless communication between the transmitter and the receiver from the first communication channel to the second communication channel when the determination unit determines that the second communication channel is available,
the adjacent communication channels are communication channels each of which has a use frequency band partially overlapping that of the second communication channel and is not accepted as a communication channel to use in the channel setting switch.

2. The wireless image communication system according to claim 1, wherein
the determination unit is included in the transmitter, and
the transmitter communication unit transmits the information related to the second communication channel to the receiver when the determination unit determines that the second communication channel is available.

3. The wireless image communication system according to claim 2, wherein the transmitter or the receiver further comprises a notifying unit configured to notify the operator of the fact that it is difficult to change the communication channel to use to the second communication channel when the determination unit determines that the second communication channel is not available.

4. The wireless image communication system according to claim 1, wherein
the determination unit is included in the receiver, and
the receiver communication unit transmits information indicating that the second communication channel is available to the transmitter when the determination unit determines that the second communication channel is available.

5. A wireless image communication apparatus for an endoscope apparatus, comprising:
a communication unit configured to receive image data wirelessly transmitted from a transmitter by a first communication channel and receive information of changing a communication channel to use from the first communication channel to a second communication channel from the transmitter during reception of the image data; and
a determining unit configured to perform a detection of a use state of each of the second communication channel and adjacent communication channels and to determine whether or not the second communication channel is available based on a result of the detection when the communication receives the information, and
a process of changing a communication channel to use in wireless communication with the transmitter from the first communication channel to the second communication channel is performed when the determination unit determines that the second communication channel is available,
the adjacent communication channels are communication channels each of which has a use frequency band partially overlapping that of the second communication channel and is not accepted as a communication channel to use in the channel setting switch.

6. A wireless image communication apparatus for an endoscope apparatus, comprising:
a communication unit configured to wirelessly transmit image data to a receiver by a first communication channel;
a channel setting switch configured to set a communication channel to use in a wireless communication with the receiver related to a transmission of the image data;
a communication unit configured to wirelessly transmit the image data to the receiver; and
a determination unit, wherein, when a second communication channel, which is different from a first communication channel that has been set, is newly set, the determination unit performs a detection of a use state of each of the second communication channel and adjacent communication channels and determines whether or not the second communication channel is available based on a result of the detection,
wherein, when the determination unit determines that the second communication channel is available, then a communication channel to use in a wireless communication with a transmitter and the receiver from the first communication channel to the second communication channel,
the adjacent communication channels are communication channels each of which has a use frequency band partially overlapping that of the second communication channel and is not accepted as a communication channel to use in the channel setting switch.

* * * * *